United States Patent
Haase et al.

(10) Patent No.: US 7,552,644 B2
(45) Date of Patent: Jun. 30, 2009

(54) DEVICE FOR DETERMINING STRAINS ON FIBER COMPOSITE COMPONENTS

(75) Inventors: Karl-Heinz Haase, Pfungstadt (DE); Carsten Hecker, Darmstadt (DE); Sebastian Klein, Munich (DE); Sigmund Glaser, Munich (DE)

(73) Assignee: Hottinger Baldwin Messtechnik GmbH, Darmstadt (DE)

( * ) Notice: Subject to any disclaimer, the term of this patent is extended or adjusted under 35 U.S.C. 154(b) by 0 days.

(21) Appl. No.: 10/577,635

(22) PCT Filed: Oct. 29, 2004

(86) PCT No.: PCT/EP2004/012310

§ 371 (c)(1),
(2), (4) Date: Apr. 9, 2007

(87) PCT Pub. No.: WO2005/043107

PCT Pub. Date: May 12, 2005

(65) Prior Publication Data
US 2008/0034881 A1      Feb. 14, 2008

(30) Foreign Application Priority Data
Oct. 30, 2003   (DE) ............................... 103 50 974

(51) Int. Cl.
*G01B 7/16* (2006.01)
(52) U.S. Cl. .......................................... 73/768; 73/760
(58) Field of Classification Search ................. 73/768, 73/760
See application file for complete search history.

(56) References Cited

U.S. PATENT DOCUMENTS

| | | | |
|---|---|---|---|
| 4,307,371 A * | 12/1981 | Ort | 338/2 |
| 4,731,694 A | 3/1988 | Graebner et al. | |
| 4,849,668 A * | 7/1989 | Crawley et al. | 310/328 |
| 5,377,548 A | 1/1995 | Ballivy | |
| 5,631,622 A | 5/1997 | Hauber et al. | |
| 5,723,792 A * | 3/1998 | Miyazaki | 73/769 |
| 5,747,698 A * | 5/1998 | Spillman et al. | 73/780 |
| 5,978,693 A * | 11/1999 | Hamilton et al. | 600/391 |
| 6,370,964 B1 | 4/2002 | Chang et al. | |
| 6,399,939 B1 | 6/2002 | Sundaresan et al. | |
| 6,555,767 B1 * | 4/2003 | Lockery et al. | 177/211 |
| 6,769,313 B2 * | 8/2004 | Weiss | 73/862.046 |
| 6,909,919 B2 * | 6/2005 | Jain et al. | 607/119 |
| 7,043,997 B2 * | 5/2006 | Mattson et al. | 73/800 |

(Continued)

FOREIGN PATENT DOCUMENTS

DE      35 20 664      12/1986

(Continued)

*Primary Examiner*—Max Noori
(74) *Attorney, Agent, or Firm*—W. F. Fasse; W. G. Fasse (57) ABSTRACT

In an apparatus for determining loads on fiber composite components (1), especially of vehicle and aircraft parts, strain gages (3) are integrated in the components (1) for determining strains. The strain gages (3) are connected with an evaluating apparatus (4), for monitoring and determining loads that tend to cause damage. The strain gages (3) are preferably integrated into the fiber composite component (1) such that the measuring grids (5) thereof are laid between individual fiber layers (2) and are guided out of the component (1) ready for connection via special connecting pins (8) to the associated evaluating apparatus (4) via loose cable connections (12).

16 Claims, 4 Drawing Sheets

U.S. PATENT DOCUMENTS

| | | | |
|---|---|---|---|
| 7,083,199 B2 * | 8/2006 | Graber et al. | 280/782 |
| 2002/0021058 A1 | 2/2002 | Duerr | |
| 2004/0046380 A1 | 3/2004 | Graber et al. | |
| 2004/0183648 A1 * | 9/2004 | Weber et al. | 338/47 |

FOREIGN PATENT DOCUMENTS

| | | |
|---|---|---|
| DE | 36 42 780 | 11/1987 |
| DE | 40 21 914 | 1/1991 |
| DE | 40 25 564 | 9/1991 |
| DE | 199 23 143 | 11/2000 |
| EP | 0 667 514 | 8/1995 |
| WO | WO 95/14917 | 6/1995 |
| WO | WO 97/19325 | 5/1997 |
| WO | WO 01/39253 | 5/2001 |
| WO | WO 03/039894 | 5/2003 |

* cited by examiner

DEVICE FOR DETERMINING STRAINS ON FIBER COMPOSITE COMPONENTS

FIELD OF THE INVENTION

The invention relates to an apparatus for the determination of loads on fiber composite components as well as production methods thereof and a pick-up or sensor element for the apparatus.

BACKGROUND INFORMATION

Ever more components of fiber composite materials are used in the construction of vehicles and aircraft. These fiber composite materials preferably consist of glass, carbon or aramid fibers, which are built-up of fiber layers and connected with one another through polymer materials. In that regard, the components are generally produced through lamination of the synthetic resin impregnated fiber layers under pressure and heat in a pressing form or mold. These composite materials are usually lighter than comparable metal structural parts and possess a high stiffness and strength and are therefore preferably utilized in aircraft construction.

For such structures, the exact documentation of the operational loads is of great interest, in order to prove or document the remaining operating life of the structure as near as possible to actual reality. In this manner, the permissible operating times for each structure can be fully utilized in an economically optimal manner. For that purpose it is primarily necessary to record and to document the prevalence and the magnitude of the structural deformations. These are summarized to load collectives and correlated with the determined operating life of the material. Thereby, on the one hand the maintenance and service intervals and on the other hand the remaining operating life can be adapted to the conditions that actually arose during operation, and thus the structure can be operated in an economically optimal manner.

Moreover, damages such as cracks or delaminations can arise in the material of lightweight structures due to high loads or through too-high production tolerances, such as shrinkage voids or sink holes or fiber proportions or components. These damages can considerably weaken the mechanical stiffness and the strength of the components. Especially in connection with aircraft, such components are also subjected to the danger of impact damages through birds and ice particles during operation. These loads can lead to previously mentioned damages within the composite materials, which are not externally visible and represent an endangerment of safety. In order to be able to detect or determine such damages, it is known to recognize these in the regularly occurring maintenance procedures, through non-destructive testing methods such as x-ray or ultrasound tests. However, in that regard the danger exists, that a clear reduction of the operating strength arises until the time of the next maintenance inspection due to damage growth as a result of high vibration or oscillation loads, whereby such reduction of the operating strength is to be avoided in all cases. Therefore, a series of possibilities exists, to detect such dangers immediately especially on aircraft components, in order to remove or correct the damages as early as possible.

Often, however, it is also necessary to inspect such components or other fiber composite material components before the installation or utilization in the aircraft construction and the like, in order to determine the operating life and to avoid constructive damages tending to cause danger. In that regard it is necessary to impose prescribed loads on the components that are to be inspected or examined, in order to prepare a proof or documentation of the operating life and to determine strains tending to cause damages on the components and to recognize a danger of damage at an early time. In that regard, the method for the monitoring and for the examination primarily distinguishes itself through the evaluation and in the attainment of the measuring results in the form of a loading analysis.

An apparatus for the determination of impact damages on fiber composite material components is known from the DE 40 25 564 C1. For that purpose, a plurality of distributed arranged piezoelectric foil elements are secured on an outer surface side of the vehicle body components that are usually only a few millimeters thick, and are lead to an electronic monitoring arrangement via an electrical connection. Upon the occurrence of a strong compression influence through an impact loading, which can lead to a delamination, a capacitive charge variation arises in the piezo transducer elements arranged in the proximity, whereby the capacitive charge variation is essentially proportional to the impact pressure. This charge variation is then detected in a monitoring arrangement and can be indicated corresponding to the damage-relevant impact pressure and location, in order to immediately introduce a targeted damage examination. However, with such a monitoring apparatus, only excessive impact loadings that can lead to a delamination are detectable. An exact documentation of the operating loads for the evidence or proof of the remaining operating life, as well as damages on the fiber composite material components that arise through other excessive strain loads that are not dependent on pressure, are not detectable with this monitoring apparatus. Especially, with such a monitoring apparatus for examination purposes, only impact loadings on prescribed construction parts can be analyzed.

It is known to apply an optical reflection diffraction grating on a fiber composite material, from the DE 35 20 664 A1. For monitoring the surface strain, the reflection grating can be illuminated with a laser light beam, and the radiation intensity thereof in a certain reflection direction can be detected. If the surface of the material changes due to a strain expansion or compression, thereby the diffraction angles and thus also the radiation intensity in the detected directions also change. Such a radiation intensity is then measured with opto-electronic position detectors, and can be indicated as a value of the surface strain. Such a monitoring of the material surfaces is, however, only possible where this surface can be radiated with laser light and the reflected or re-radiation intensity thereof is detectable at a certain spacing distance from the surface. Especially when the surfaces are additionally provided with other protective or insulation layers, which do not follow the strain, then such a monitoring or a strain examination cannot be carried out.

The detection of a surface strain with strain gages on a rotational shaft of a fiber composite material is known from the DE 40 21 914 C2. This strain measurement is carried out for the rotational moment or torque determination by means of a testing machine, whereby the strain gages are glued or adhesively applied onto the surface of a fiber composite pipe, and the strain detection thereof serve for the calculation of the torque in the torsional body. For that purpose, apparently commercially available typical strain gages are used, which are not suitable for measurements of strain tending toward damage on fiber composite material surfaces, because typical commercially available measuring grids do not withstand such strain regions. Moreover it is not known, that the determination of the rotational moment or torque is utilized for the proof or evidence of the remaining operating life of the component.

Therefore, such typical commercially available strain gages would have to be renewed after each examination test run or each loading with surface strains tending to cause damage, which brings about a considerable cost-intensive expense and effort especially in connection with multi-point measurements. Especially, in material analysis measurements, no measured values could further be evaluated in the upper damage-inducing range, so that thereby also only an inadequate analysis result can be achieved. While it is conceivable to produce special strain gages of wire measuring grids for such surface tension measurements, which wire measuring grids also withstand greater strain ranges on composite fiber surfaces, which would be uneconomical, however, for multi-point measurements for component analysis or for the monitoring of large surface area aircraft parts.

Strain gages and methods for their production are, however, previously known from the EP 0 667 514 B1. These basically consist of a typical commercially available photolithographically produced measuring grid that is vapor deposited on a carrier film and additionally is covered with a protective layer. For the connection, this measuring grid has flat soldering connection surfaces, which represent the beginning and the end of the measuring grid. Connection wires are soldered thereon for the wiring, and are lead to the provided connection parts for the circuit-connection. Such a strain gage can basically be applied only on the surface of a strain body, because otherwise a subsequent wiring-connection is no longer possible. A previous wiring-connection would also be unrealistic, because an economical handling of a plurality of connection wires is hardly possible in the known production methods of composite materials.

SUMMARY OF THE INVENTION

Therefore, it is the underlying object of the invention to provide an apparatus for the measurement of material tensions on fiber composite materials as well as cost-advantageous transducer or sensor elements that are suitable therefor, and that are especially suitable for multi-point measurements or for the large-surface monitoring of such components.

This object is achieved by the invention set forth herein.

The invention has the advantage, that due to the integration of the strain gages near the neutral fiber of the composite materials, very flat nearly typical commercially available foil measuring grids can be utilized, whereby these foil measuring grids are not also destroyed by the material loads even in connection with high surface tensions of the composite materials. Thereby, cost-advantageous or economical multi-point measurements are also possible on composite materials, which can be utilized both for the analysis of the material components as well as for the load monitoring and for the longterm continuous monitoring of large surface area components preferably of aircraft body components.

The invention simultaneously has the advantage, that due to the integration of the strain gages, these can immediately be utilized in the workshop in the production of the composite material components. Thereby, the pick-up or sensor elements are also simultaneously protected against external damages during the component assembly or installation, maintenance, and in operation. Due to the flat foil measuring grids of the strain sensors, these can be inserted in a space-saving manner between the individual composite layers, whereby advantageously the matrix structure of the components is basically not weakened, and additionally a force-transmitting connection between the sensor elements and the strain-relevant composite materials is achievable. Since such a connection is also achieved on both sides, only small hysteresis effects arise in the measuring operation, so that high measuring accuracies can be achieved.

The sensor elements according to the invention have the advantage, that nearly all loading types on fiber composite materials are detectable in a cost-advantageous or economical manner during the operating time using typical commercially available foil measuring grids. An advantageous integration possibility is simultaneously achieved through the provided connecting pins, through which a subsequent wiring-connection via plug connections is made possible. The embodiment according to the invention with the provided connecting pins especially allows a high degree of automation in the integrated composite material production, because connection wires that are to be lead out do not need to be taken into account in the production technique, and nonetheless a subsequent quick connection possibility is provided.

BRIEF DESCRIPTION OF THE DRAWINGS

The invention will be explained more closely in connection with an example embodiment, which is illustrated in the drawing. It is shown by.

DETAILED DESCRIPTION OF EXAMPLE EMBODIMENTS OF THE INVENTION

Figure 1:
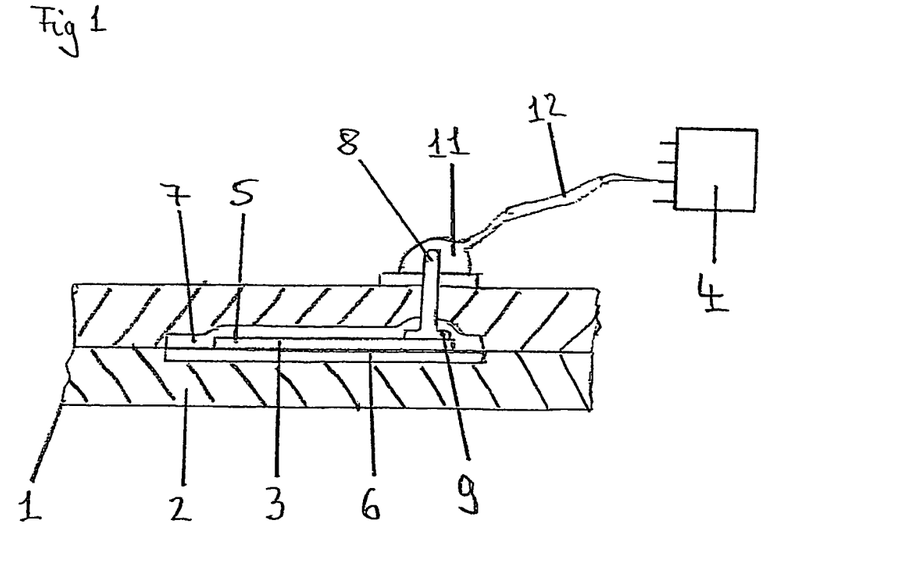
FIG. 1: an apparatus for the determination of strains on a fiber composite material component.

FIG. 1 of the drawing shows, in a partial cut-out section manner, an apparatus for the determination of a strain or for the inspection and for the load monitoring on a fiber composite material component 1 with a foil strain gage 3 integrated in the fiber layers 2 and with a connected evaluating apparatus 4.

The fiber composite material component 1 is illustrated only in a partial cut-out portion, of a fiber composite material consisting of only two layers 2, between which the strain gage 3 is arranged. Such fiber composite materials 1 generally consist of plural layers, preferably of glass, carbon or aramid fiber plies. These are usually laid one on top of another and are impregnated by means of a polymeric material, and are thereby fixedly or rigidly connected with one another. Depending on the desired strength requirements, fiber layers are laid one on top of another and are oriented in the force and tension direction.

Such fiber composite material components are usually embodiable as thin formed bodies or plates or panels in thicknesses of 1 to 50 mm with rib reinforcement or in sandwich construction in complex configurations. These are preferably utilized in the aircraft and vehicle industry as lightweight, form stable structural components, which are largely independent of aging effects and are corrosion resistant and can be utilized as an alternative to typical conventional metallic materials. For such components, the recording of the operating loads is of great interest, in order to be able to document or prove the operating life of the structure in a manner that is as near as possible to actual reality. In this manner, the permissible operating times for each structure can be fully utilized in an economically optimal manner. For that purpose, primarily the prevalence and the magnitude of the structural deformations are recorded and documented by the evaluating apparatus 4.

Moreover, the apparatus can be used in order to determine damages in such components at an early time, whereby such damages are not externally recognizable and represent an endangerment potential.

In that regard, fiber breaks, a matrix failure, a delamination, or debonding damages can arise in the interior of the composite materials, which damages can all be determined through their strain behavior. However, before use of these composite materials, often also operating lifetime tests and strength analyses must be carried out, in which the components are loaded in such a targeted manner, so that fatigue ruptures or breaks and also damage-relevant strains arise, in order to be able to determine the permissible application purposes. In such component monitorings or examinations, however, surface strains arise, which cannot be carried out with typical foil strain gages, because the strain capacity of typical conventional measuring grids is exceeded by such high strains.

For that reason, the invention starts from the recognition, to integrate the foil measuring grids largely or substantially in the so-called neutral fiber, approximately in the middle of the material thickness in the composite material 1, at which the strain-induced bending tensions especially in connection with loads tending to cause damages, are the lowest. Furthermore, in this integration, a connection on both sides of the strain gages 3 with the composite material 1 is possible, which especially minimizes the hysteresis effect, so that thereby very exact measurements, operating load determination and monitorings can be carried out. For that purpose, in the production of the composite materials 1 especially for the monitoring on large surface area aircraft components, a plurality of such strain gages 3 are already integrated in the factory or workshop, so that the strain gages 3 are positioned or placed at prescribed spacing distances so that nearly all damage types are determinable or detectable at an early time. Thereby the danger of aircraft crashes can be considerably reduced. In the monitoring or examination of such components, the spacing distances of the strain gages 3 to be used can differ depending on the loading relevance of the components, and can be optimally distributed according empirical examinations or loading calculations.

Such a monitoring apparatus is shown in FIG. 1 of the drawing in a schematic and partial cut-out manner, in which all of the strain gages 3 arranged on the component 1 are connected to an electronic evaluating apparatus 4 for the control or inspection and for the load monitoring. The same arrangement arises basically also in an examination or testing apparatus in which the components 1 are impacted or loaded up to a load that tends to cause damage, in order to analyze the loading limits or the damage-tending construction prerequisites. Both apparatuses basically distinguish themselves simply with respect to their evaluation, whereby for the testing or examination apparatus an electronic evaluating apparatus is provided that especially takes into account the prescribed loads at the determined strain, while the load monitoring and control apparatus reaches a conclusion as to the operating lifetime or as to the damage or a load tending to cause damage simply from the determined strain values. Thus, in the illustrated monitoring apparatus, preferably strain variations or changes are detected and indicated according to type, location, prevalence and magnitude, or are signaled as a damage danger, in the electronic evaluating apparatus 4. In that regard, the strain gage 3 illustrated in FIG. 1 of the drawing essentially consists of a measuring grid 5, that is applied on a carrier layer 6, as this is shown in more detail individually in FIG. 2 of the drawing. The carrier material 6 is electrically insulating and temperature resistant, whereby preferably a polymeric material such as polyimide is used. For improving the adhesion in the later structural integration, the outer surface of the carrier material 6 is radiated and activated. The measuring grid 5 is provided with the carrier material 6 on both sides, namely is also covered with a carrier layer 7 on the top side.

Figure 2:
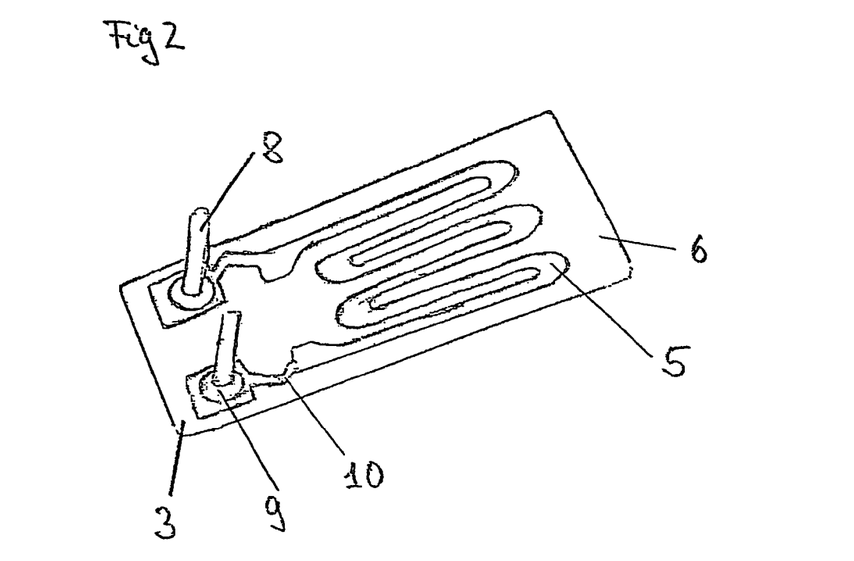
FIG. 2: a strain gage for the integration in a fiber composite material part.

The measuring grid 5 is electrically conductively connected with two connecting pins 8, that are arranged perpendicularly to the measuring grid 5. For that purpose, the connecting pins 8 are preferably soldered with the measuring grid 5 via a contact base or pad 9. For that purpose, the connecting pins 8 have a wider base or pedestal portion at the end and preferably a height of approximately 5 to 20 mm. The connecting pins 8 are connected with the measuring grid 5 via a tension or strain relief 10. The strain relief 10 represents a portion or region in which the conductor path is embodied as a loop, so that in connection with a strain of the strain gage 3, the cross sectional area of the conductor path and therewith the electrical resistance thereof does not change.

Figure 3:
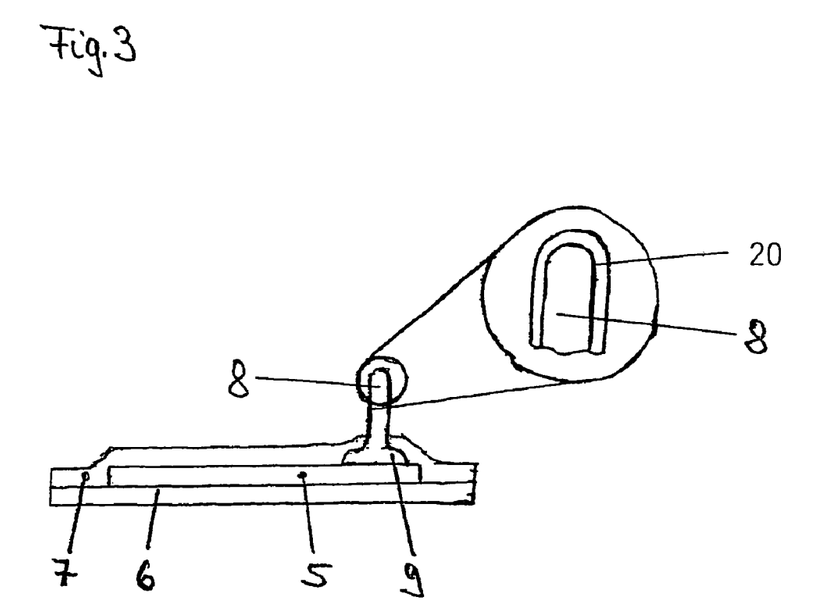
FIG. 3: a side view of a strain gage for the integration in a fiber composite material part with an enlarged cut-out section of a connecting pin.

In FIG. 3 of the drawing, the special strain gage 3 consisting of a measuring grid 5 and two carrier layers or substrates 6 and 7 is illustrated in a side view, whereby especially the embodiment or construction of the contact pins 8 is depicted enlarged in a side illustration. From that it can be seen that the contact pins 8 during their production are provided with an insulating protective layer 20, in order to prevent a current flow that falsifies the measurement value, in connection with electrically conducting composite layer materials 1 such as, for example, carbon fibers. This insulating layer 20 is preferably of a polymeric temperature resistant material. In a particular embodiment of the invention, the embodiment forms of the strain gages 3 as pick-up or sensor elements can also be produced as rosettes. Moreover, this embodiment of the strain gages 3 can also be used for other sensor elements, which are integratable in fiber composite materials 1, such as piezo fiber modules.

For contacting with a connecting post or pad 11, this insulating layer is removed or scraped off by provided clamp or terminal edges of the connecting post or pad 11 during the plugging-on process, in order to lead it to the electronic evaluating apparatus 4 via a cable connection 12 that is to be produced subsequently. In the evaluating apparatus 4, the individual strain gages 3 are first circuit-connected to a Wheatstone bridge, in order to be able to evaluate the detected strains, Similarly, also the remaining strain gages, which are not shown, in the other fiber composite material areas are lead to the electronic evaluating or monitoring apparatus 4. Thereby, in connection with the monitoring in an aircraft, even up to a few hundred of such sensor elements 3 can be circuit-connected to the evaluating or monitoring apparatus 4, by which, during the flight operation, both the load magnitudes as well as the exceeding of prescribed load limits is displayable or signalable in a location allocated manner. Such apparatuses can, however, also be utilized for tension analyses in connection with prescribed load progressions. In large surface area aircraft components it is partially necessary in connection with the tension analysis, to provide several thousand of such strain gages 3 as sensor elements in the components that are to be tested, in order to be able to evaluate an exact loading behavior. For that purpose, especially a subsequent solder-free contacting possibility via connecting posts or pads 11 that are able to be plugged-on and an integration into the composite material parts 1 in the fabrication facility are advantageous.

Figure 4:
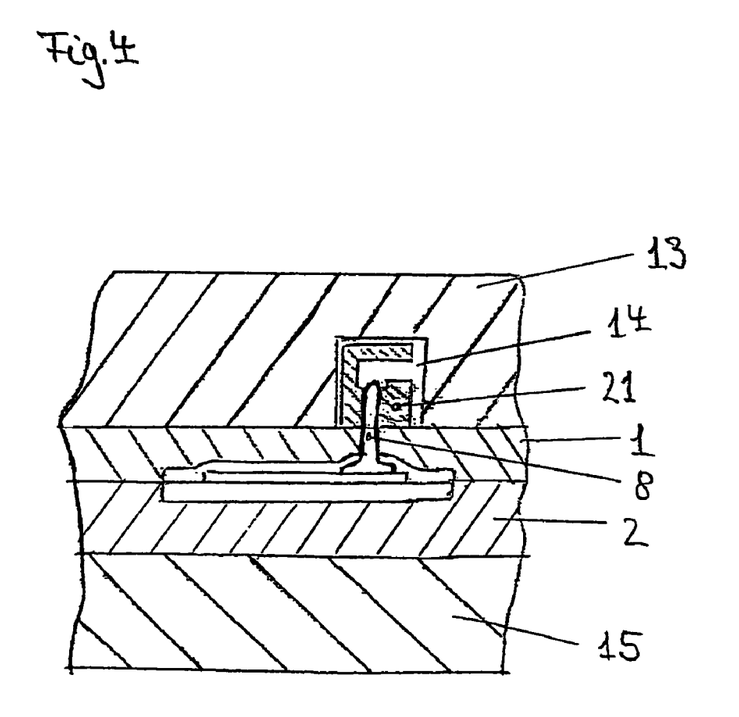
FIG. 4: a strain gage with fixed connection post in two mold halves.

However, in the fabrication facility, it is also already possible to apply fixed or rigid contact posts or pads 21 onto the contact pins, as this is illustrated in the embodiment according to FIG. 4 of the drawing. In that regard, during the production of the composite material 1, a recess 14 is provided in one of the two mold halves 13, into which the contact post or pad 21 can be inserted. During the subsequent pressing process for the fabrication of the composite material part 1, now the fixed connecting post 21 is pressed onto the respective contact pin 8, and thus establishes a fixed electrical connection thereto. This fixed connecting post 21 can subsequently be electrically connected via plug-in contacts with the evaluating apparatus 4.

Figure 5:
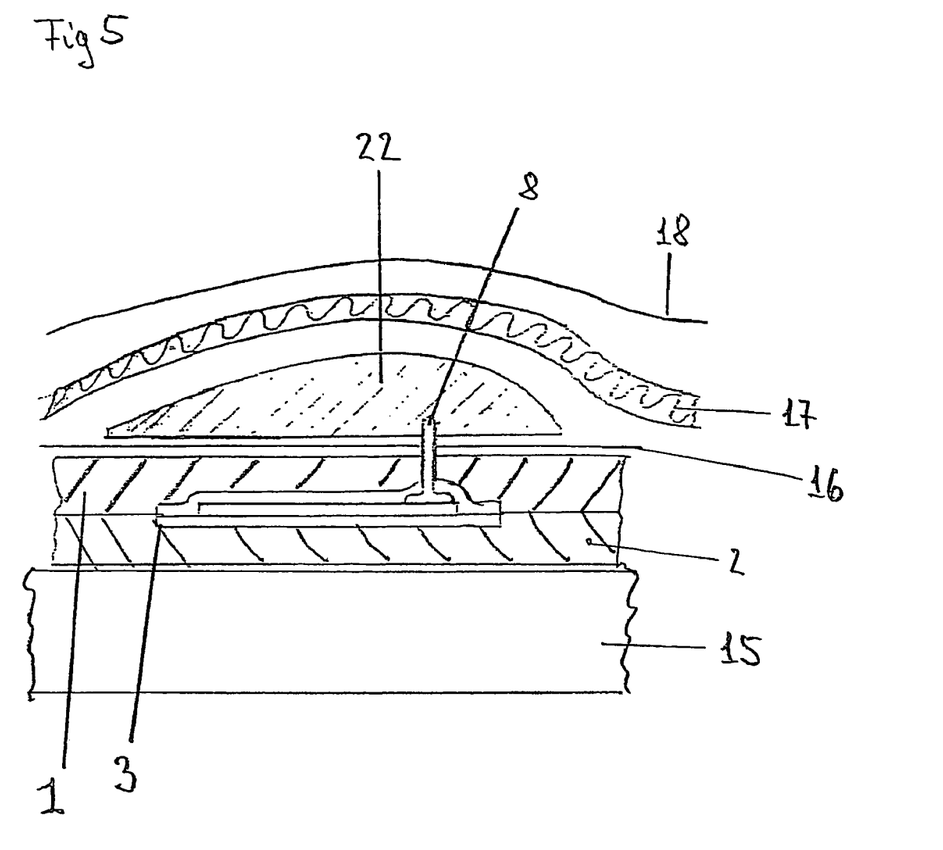
FIG. 5: an integration process of a strain gage in a fiber composite material part within a workpiece mold.

A further production process for the integration of the strain gages 3 as sensor elements is illustrated in FIG. 5 of the drawing. For that purpose, a known pressure or vacuum process is used for the production of the composite material components 1. In that regard, the fiber layers 2 are laid one after another into a prescribed mold 15, and the sensor elements 3 are placed therebetween, or already before are already connected with the respective fiber layer 2. Thereby it is not significant whether the fiber material 2 is dry or was already impregnated with resin. The strain gage 3 is to be laid into the fiber material 2 in such a manner so that the connecting pins 8 protrude outwardly on one side out of the fiber material 2. A forming stamp or stamping die 22 of a soft porous material such as preferably foam material, is pressed under light pressure over the connecting pins 8. Thereby, the stamping die 22 protects the connecting pins 8 during the production of the fiber composite component 1 and thereby also simultaneously fixes the strain gages 3. After the production process, the stamping die 22 can be removed. Beside the stamping die 22, the typical auxiliary materials for the production of fiber composite components 1 can be utilized, like the provided peel-off film 16 as well as the suction mesh 17 with the vacuum film 18.

Figure 6:
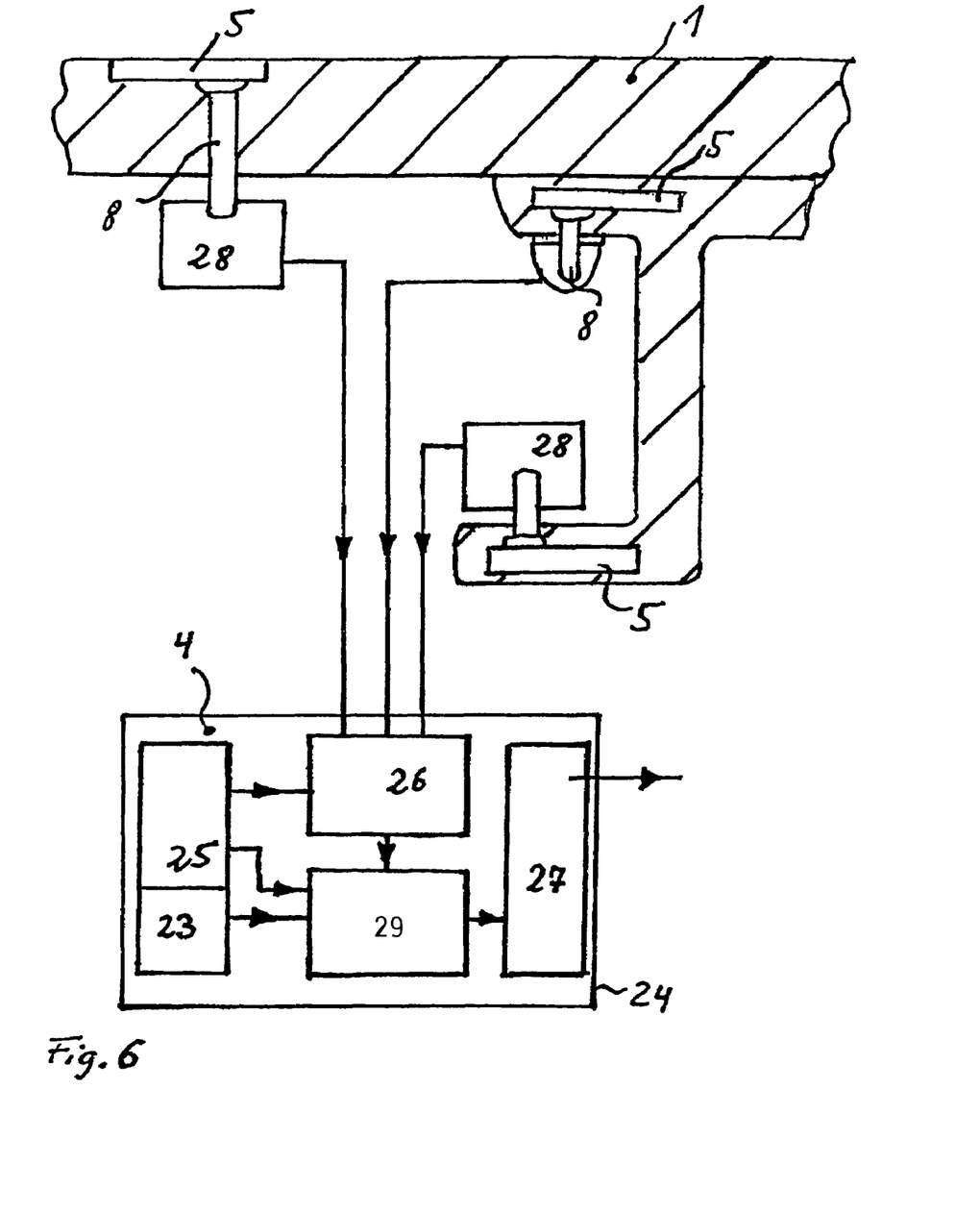
FIG. 6: a further preferred example embodiment of the apparatus with several integrated measuring points.

FIG. 6 shows a further preferred example embodiment of the invention with several integrated strain gages 3. Three strain gages 3 with measuring grids 5 are integrated at various different locations of the structure of fiber composite material 1 in various different layers. The FIG. 6 shows the cross-section through the structure, which consists of a cover skin and an inwardly arranged stiffening rib. For the identification of the measuring locations, the contact pins 8 are used to secure an electrical unit 28 on the inner side of the structure, with the help of which electrical unit 28 the evaluating apparatus 4 can identify the measurement locations. The evaluating apparatus 4 includes a shielded housing 24 and a current source 25. The measurement signals are amplified with an electrical module or amplifier unit 26 and delivered to a data processor 29, which processes the current measured value and stores it in the memory unit 27. Additionally, the evaluating apparatus 4 is equipped with an internal timer 23, so that the magnitude and the prevalence of strain conditions in the structure can be recorded. Additionally, the current measured value can be compared with reference signals and thereby the exceeding of limit values can be recognized. The stored data can be read-out for example during the service, and the data can be evaluated for the proof of the remaining service life of the structure.

The invention claimed is:

1. An arrangement for determining loads on a fiber composite component, comprising:
    a fiber composite component including plural fiber layers comprising a fiber composite material; and
    at least one strain sensor unit, which strain sensor unit comprises a foil strain gage including a measuring grid covered with insulating layers on both opposite sides of said measuring grid, and which strain sensor unit further comprises electrical connecting pins electrically conductively connected to and extending perpendicularly from said measuring grid;
    wherein:
    said at least one strain sensor unit is respectively integrated into said fiber composite component in that said strain gage is sandwiched between at least one of said fiber layers on a first side of said strain gage and at least one of said fiber layers on a second side of said strain gage opposite said first side, and said connecting pins extend perpendicularly through and protrude outwardly from said at least one fiber layer on at least one of said sides of said strain gage so that respective contact portions of said connecting pins are externally accessible for making electrical contact therewith outside of said fiber layers of said fiber composite component.

2. The arrangement according to claim 1, wherein said at least one strain sensor unit comprises a plurality of said strain sensor units arranged at prescribed locations spaced apart from one another in said fiber composite component.

3. The arrangement according to claim 1, wherein said strain gage respectively of said at least one strain sensor unit is sandwiched between said fiber layers approximately at a middle of a thickness of said fiber composite component adjacent to a bending-strain-neutral one of said fiber layers.

4. The arrangement according to claim 1, further comprising insulating layers provided on said contact portions of said connecting pins, wherein said insulating layers are easily removable so as to allow external electrical connection to said contact portions.

5. The arrangement according to claim 1, wherein said connecting pins each have a length of 5 to 50 mm and a diameter of 0.5 to 2 mm.

6. The arrangement according to claim 1, further comprising fixed contact posts that lie in an insulated manner on an outer surface of an outermost one of said fiber layers, and that are electrically conductively mounted on said contact portions of said connecting pins, and that are adapted to serve for establishing a releasable electrical connection to an external electrical apparatus.

7. The arrangement according to claim 1, further comprising an evaluating apparatus that is electrically conductively connected to said contact portions of said connecting pins, wherein said foil strain gage is adapted to provide via said connecting pins to said evaluating apparatus an electrical signal indicative of a strain value in said fiber composite component at a measuring location of said foil strain gage, and wherein said evaluating apparatus includes an electronic computing apparatus adapted to determine from said electrical signal a location-allocated strain value of said fiber composite component.

8. The arrangement according to claim 7, wherein said evaluating apparatus is a load monitoring apparatus that further includes a memory adapted to store samples of said location-allocated strain value that varies over time.

9. The arrangement according to claim 8, wherein said load monitoring apparatus further includes a comparator adapted to compare said samples of said location-allocated strain value to at least one load limit value, and a display or signaling arrangement adapted to display or signal an information indicative of damage danger or actual damage of said fiber composite component if at least one of said samples of said location-allocated strain value exceeds said at least one load limit value.

10. The arrangement according to claim 7, wherein said evaluating apparatus is a testing apparatus adapted to couple said location-allocated strain value with data regarding test loads applied to said fiber composite component and based thereon to produce a loading or tension analysis of said fiber composite component being tested.

11. The arrangement according to claim 7, wherein said electronic computing apparatus includes a processor adapted to evaluate said electrical signal with respect to at least one criterium selected from the group consisting of a probability, a prevalence distribution, a polarity and a time sequence, in order to determine said location-allocated strain value.

12. The arrangement according to claim 7, wherein said electronic computing apparatus includes a processor, and said evaluating apparatus further comprises an electrically shielded housing, an electrical power supply, an amplifier unit, an internal timer, and a data memory.

13. The arrangement according to claim 7, further comprising an electrical device adapted to identify said measuring location of said foil strain gage in said fiber composite component, and wherein said electrical device is electrically connected and interposed between said evaluating apparatus and said contact portions of said connecting pins.

14. A sensor element for determining strains in a fiber composite component, comprising a foil strain gage with a measuring grid, arranged between a carrier layer and an upper cover layer, connecting pins extending perpendicularly to the measuring grid and serving as electrical connection points, and strain relief elements formed of a material of the measuring grid respectively connected between ends of the measuring grid and the connecting pins, wherein the upper cover layer is formed of a same material as the carrier layer, and wherein the strain relief elements are adapted to relieve material strains from a fiber composite material of the fiber composite component so as to be adapted to prevent falsification of a resistance value measurement of the measuring grid by a strain-varied resistance influence of an electrical supply connection through the connecting pins and the strain relief elements to the measuring grid.

15. A sensor element for determining strains in a fiber composite component, comprising a foil strain gage with a measuring grid, arranged between a carrier layer and an upper cover layer, and connecting pins extending perpendicularly to the measuring grid and serving as electrical connection points, wherein the upper cover layer is formed of a same material as the carrier layer, and wherein outer surfaces of the carrier layer and of the upper cover layer are roughened by irradiation to be adapted to improve an adhesion of the outer surfaces with respect to fiber layers of the fiber composite component.

16. A method of producing an arrangement for determining loads on a fiber composite component, comprising the steps:
 a) laying at least one fiber layer comprising fiber material into a mold;
 b) providing a polymeric material in or on said at least one fiber layer;
 c) placing onto said at least one fiber layer, at least one sensor unit that comprises a foil strain gage including a measuring grid and that further comprises connecting pins electrically conductively connected to and extending perpendicularly from said foil strain gage;
 d) covering said measuring grid respectively of said at least one sensor unit with at least one further fiber layer comprising fiber material such that said connecting pins protrude outwardly above said at least one further fiber layer;
 e) providing a peel-off film on said at least one further fiber layer;
 f) arranging a stamping pad of soft porous material above said peel-off film so as to receive respective outwardly protruding portions of said connecting pins;
 g) pressing a layered stack including said stamping pad, said peel-off film, said at least one further fiber layer, said at least one sensor unit, said polymeric material, and said at least one fiber layer against said mold, wherein said pressing is achieved by a vacuum process or a pressure process, so as to form a solidified or rigidified fiber composite component having said foil strain gage integrated therein and having portions of said connecting pins protruding outwardly therefrom; and
 h) removing said stamping pad.

* * * * *